(12) United States Patent
Stinson

(10) Patent No.: US 7,354,455 B2
(45) Date of Patent: *Apr. 8, 2008

(54) MEDICAL STENT WITH A VALVE AND RELATED METHODS OF MANUFACTURING

(75) Inventor: Jonathan S. Stinson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/911,650

(22) Filed: Aug. 5, 2004

(65) Prior Publication Data

US 2005/0065614 A1 Mar. 24, 2005

Related U.S. Application Data

(63) Continuation of application No. 09/972,054, filed on Oct. 9, 2001, now Pat. No. 6,790,237.

(51) Int. Cl.
*A61F 2/04* (2006.01)

(52) U.S. Cl. .................. 623/23.68; 623/1.24; 623/2.17

(58) Field of Classification Search ............... 623/1.13, 623/1.24, 2.18, 23.68
See application file for complete search history.

(56) References Cited

U.S. PATENT DOCUMENTS

| | | | |
|---|---|---|---|
| 4,339,831 A * | 7/1982 | Johnson ..................... 623/2.18 |
| 4,364,127 A | 12/1982 | Pierce et al. | |
| 4,655,771 A | 4/1987 | Wallsten | |
| 4,846,836 A | 7/1989 | Reich | |
| 5,061,275 A | 10/1991 | Wallsten et al. | |
| 5,314,473 A | 5/1994 | Godin | |
| 5,855,597 A | 1/1999 | Jayaraman | |
| 6,254,642 B1 | 7/2001 | Taylor | |
| 6,264,700 B1 * | 7/2001 | Kilcoyne et al. ........ 623/23.68 |
| 6,440,164 B1 | 8/2002 | DiMatteo et al. | |
| 6,494,909 B2 | 12/2002 | Greenhaigh | |

(Continued)

FOREIGN PATENT DOCUMENTS

EP 0 808 614 A2 11/1997

(Continued)

OTHER PUBLICATIONS

Kocher, M. et al., "Esophageal Stent with Antireflux Valve for Tumors Involving the Cardia: Work in Progress," Journal of Vascular and Interventional Radiology, vol. 9, No. 6, Nov.-Dec. 1998, pp. 1007-1010.

(Continued)

*Primary Examiner*—Bruce Snow
(74) *Attorney, Agent, or Firm*—Finnegan, Henderson, Farabow, Garrett & Dunner, L.L.P.

(57) ABSTRACT

Medical stents having valves and their methods of manufacture are disclosed. The valve may be basket-shaped and formed integral to a medical stent to prevent undesirable backflow across the valve. The valve can be formed by converting the braided wires of the stent, by providing elastomeric material onto a mold or fixture to form an elastomeric valve, or by attaching a gasket valve. The valve is normally closed but configured to allow easy opening in response to a predetermined condition.

45 Claims, 5 Drawing Sheets

U.S. PATENT DOCUMENTS 6,544,291 B2    4/2003    Taylor

FOREIGN PATENT DOCUMENTS

| FR | 2 788 217 | 7/2000 |
|----|-----------|--------|
| WO | 00/32137  | 6/2000 |
| WO | 01/28459  | 4/2001 |
| WO | 02/43620  | 6/2002 |

OTHER PUBLICATIONS

PCT International Search Report in PCT/US02/29831, mailed on Jan. 22, 2003.

* cited by examiner

MEDICAL STENT WITH A VALVE AND RELATED METHODS OF MANUFACTURING

This is a continuation of application Ser. No. 09/972,054, filed Oct. 9, 2001, now U.S. Pat. No. 6,790,237, which is incorporated herein by reference.

FIELD OF THE INVENTION

The present invention relates to medical stents and methods of manufacturing the same. In particular, the present invention relates to medical stents with valves for preventing harmful gastric acid reflux in a patient.

BACKGROUND OF THE INVENTION

Medical stents are generally flexible, tubular, expandable bodies formed of a plurality of interconnecting wires. The stents are used in a wide variety of medical applications, such as treatment of esophageal diseases or reinforcing constricted blood vessels or urinary tracts. The stent is usually placed into a constricted portion of a patient's body using a delivery system, e.g. a catheter.

When a medical stent is used for treatment of an esophageal disease, such as esophageal tumor or stricture, the stent is placed at the lesion within the esophagus to maintain the esophageal lumen open. If the tumor or stricture is located near the junction between the stomach and the esophagus, the esophageal stent is often implanted across the lower esophageal sphincter (i.e. the ring-like muscle that constricts and relaxes the esophagus as required by normal physiological functions). However, the implantation of a stent across the normally-closed esophageal sphincter may hold the sphincter open unintentionally and cause harmful gastric acid reflux from the stomach into the esophagus.

In order to reduce the gastric acid reflux, it has been proposed to use an anti-reflux valve with an esophageal stent. An example of esophageal stent with an anti-reflux valve is disclosed by Köcher et al. ("Esophageal Stent with Antireflux Valve for Tumors Involving the Cardia: Work in Progress," JVIR 1998; 9:1007-1010). The anti-reflux valve of Köcher et al. is made of a pliable, soft polyurethane sleeve attached to the lower end of the stent. However, there are several problems associated with this type of stent. For example, the sleeve must be long enough to prevent the reflux and act as a barrier wall to defeat capillary flow of acid up the bore of the device. Since the sleeve must be long, greater deployment force and more complex delivery catheter designs are required. Typically, the length of the sleeve ranges from about 50 to 120 mm and requires extra length on the delivery system to envelope it in the "folded" condition prior to deployment. In addition, the sleeve may become twisted, tangled, or kinked, which may inhibit the passage of food into the stomach. The sleeve also may become reversed and pushed up into the esophagus during vomiting. In that case, it may be difficult for the sleeve to return to its properly functioning position.

SUMMARY OF THE INVENTION

To overcome the drawbacks of the prior art and in accordance with the purposes of the invention, as embodied and broadly described herein, one aspect of the invention provides an esophageal medical stent having a rigid but elastic valve formed, preferably, near a distal end portion of the stent. The valve is normally closed but configured to open in response to a predetermined condition. For an esophageal stent, the predetermined condition may be a pressure difference between the upstream and the downstream of the valve. The normally closed valve then allows easy opening of the valve when the pressure difference exceeds a predetermined threshold value. For instance, a passage of food from the esophagus into the stomach causes the pressure difference across the valve large enough to open the valve and, upon completion of the food passage, the valve returns to its normal-closed state to prevent the reflux. A reverse backflow due to, for example, vomiting, which causes a large pressure difference, may also be permitted by configuring the valve with an appropriate threshold value for the reverse backflow.

According to another aspect of the present invention, the esophageal stent of the present invention may also be used for treatment of the gastroesophageal reflux disease (GERD). GERD is a frequent backflow of harmful gastric acid from the stomach into the esophagus. When the lower esophageal sphincter inadvertently relaxes at inappropriate times, e.g. after meals, it allows acid and food particles to reflux back into the esophagus. Although most of the reflux contents return back to the stomach, the remaining gastric acid reflux irritates the wall of the esophagus and produces discomfort or pain known as heartburn. GERD, however, is a medical condition when such reflux is frequent or severe enough to cause more significant problems. In order to treat GERD, a stent having an anti-reflux valve of the present invention can be placed in the lower esophagus to prevent the harmful gastric acid reflux.

Another aspect of the present invention, therefore, is to provide a method of manufacturing a medical stent having an valve. The method includes: providing a generally tubular body formed of braided wires and having a proximal end portion and a distal end portion; extending the braided wires near the distal end portion; and deforming the extended wires to form the valve, wherein the valve is configured to be normally closed and to be open in response to a predetermined condition. The valve is formed basket-shaped and at least a portion of the valve and/or at least a portion of the tubular body are provided with a suitable covering material.

Another aspect of the present invention is to provide a method of manufacturing a medical stent having an elastomeric valve. The method includes: providing a generally tubular body; positioning a fixture proximate to a portion of the tubular body; applying an elastomeric material onto the fixture; and removing the fixture to form the elastomeric valve, wherein the elastomeric valve is configured to be normally closed and to be open in response to a predetermined condition.

In yet another aspect of the present invention, a method of manufacturing a medical stent having a gasket valve includes: providing a generally tubular body; and attaching an elastomeric gasket valve integral to a portion of the tubular body, wherein the integral gasket valve is configured to be normally closed and to be open in response to a predetermined condition.

In still another aspect of the present invention, a medical stent comprises: a generally tubular body formed of braided wires and having a proximal end portion and a distal end portion; and a normally closed valve formed from the braided wires extended from the distal end portion, wherein the valve is configured to open in response to a predetermined condition. The valve is a basket-shaped spring valve, and at least a portion of the tubular body and/or the valve is provided with a suitable covering material.

In still another aspect of the present invention, a medical stent comprises: a generally tubular body having a proximal end portion and a distal end portion; and a normally closed valve made of an elastomeric material and formed integral to the distal portion of the tubular body, wherein the elastomeric valve is configured to open in response to a predetermined condition. The elastomeric valve is basket-shaped, and at least a portion of the tubular body and/or the valve is provided with a suitable covering material.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the various embodiments of the invention and, together with the description, serve to explain its advantages and principles.

In the drawings.

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

Figure 1A:
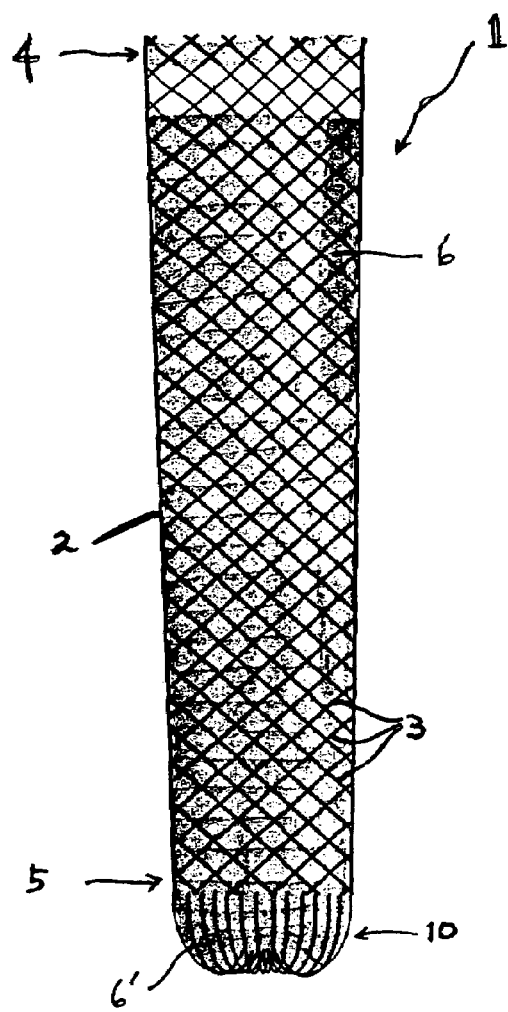
FIGS. 1A and 1B are perspective views of embodiments of medical stents with valves, according to the present invention.

Referring to FIG. 1A, a stent 1 according to an embodiment of the present invention includes a self-expanding tubular body 2 having a proximal end portion 4 and a distal end portion 5. The tubular body 2 is formed by braiding or knitting a plurality of flexible wires 3 or filaments to provide sufficient radial expansion force. The wires 3 or filaments can be made of metal, polymeric materials, composites thereof, or other suitable materials known in the art which exhibit sufficient elasticity, such as a memory material like nickel titanium alloy (i.e. nitinol). The tubular bodies 2 in the exemplary figures are of similar shape, i.e. funnel-like shape having the cross-sectional area in the proximal end portion being greater than the one in the distal end portion. The shape of the tubular bodies 2 in the exemplary figures are, however, not meant to limit or narrow the scope of the present invention. One of ordinary skill in the art would recognize that other types and shapes of tubular bodies known in the art also may be used in the practice of the present invention.

At least a portion of the tubular body 2 is provided with a strong covering 6 made of an elastic material such as polyurethane, silicone, polytetrafluoroethylene (i.e. teflon), or other suitable material exhibiting sufficient strength characteristics. The covering 6 functions primarily as a barrier to resist tumor or other tissue ingrowth.

Near the distal end portion of the tubular body 2, a basket-shaped valve 10 is formed integral to the tubular body 2. The valve 10 is normally closed to prevent acid reflux, but configured to open for the passage of food from the esophagus into the stomach. The formation of the valve 10 can be carried out before or after heat treatment, or other final manufacturing steps, of the stent 1.

Figure 2:
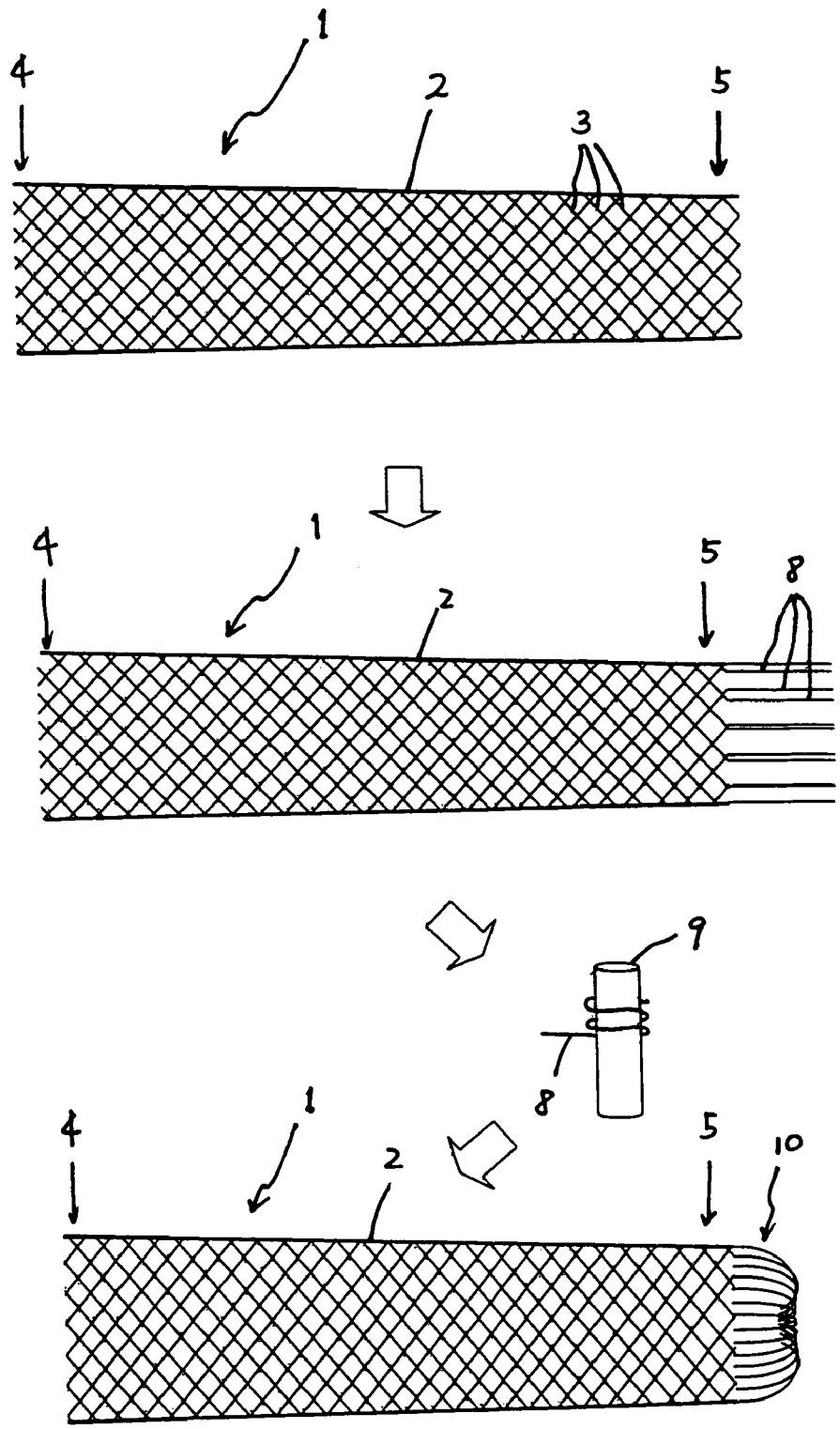
FIG. 2 is a schematic diagram showing a method of manufacturing the embodiment shown in FIG. 1A, according to an embodiment of the present invention.
Figure 3A:
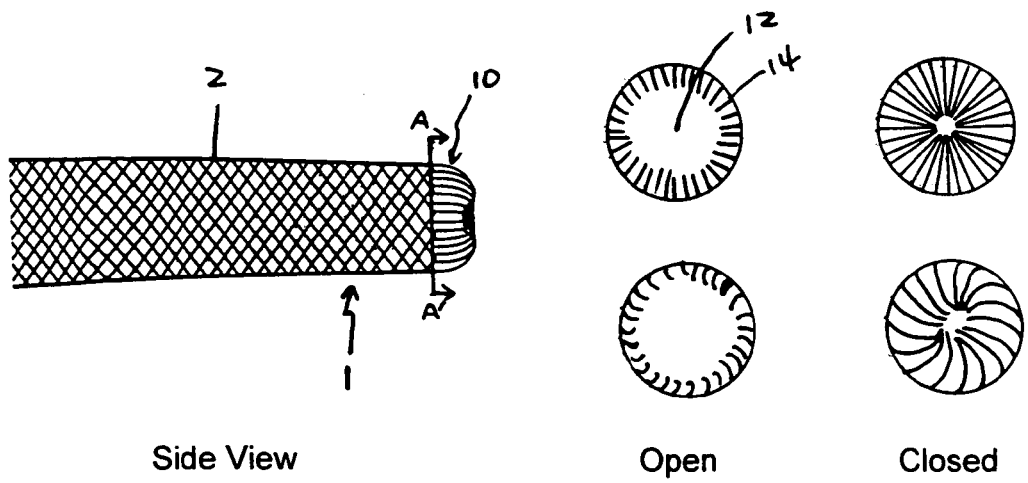
FIGS. 3A-D are side and cross-sectional views of various embodiments of medical stents with valves, according to the present invention, showing the open and closed states of the valves.

A method of forming the valve 10 according to an embodiment of the present invention is illustrated in FIG. 2. In this method, the braided wires 3 are extended from the distal end portion 5 of the tubular body 2 to form distal wires 8. The extended distal wires 8 are then deformed into a basket-shaped valve 10. Deforming the distal wires 8 is performed, for example, by curling the distal wires 8 inwards as shown in FIG. 2. Each of the distal wires 8 is wound around and then released from a cylindrical member 9 so that the distal wires 8 form a basket-shaped spring valve 10, by curling toward the center 12 of the circle 14 formed by the tubular body 2 (See FIG. 3A). FIG. 3A shows the side and distal end views of the embodiment of FIG. 1A. The distal end views include the open state (left-hand side) and closed state (right-hand side) of the valve. The lower end view figures of FIG. 3A show that the curled wires may also be curled sideways.

Figure 3B:
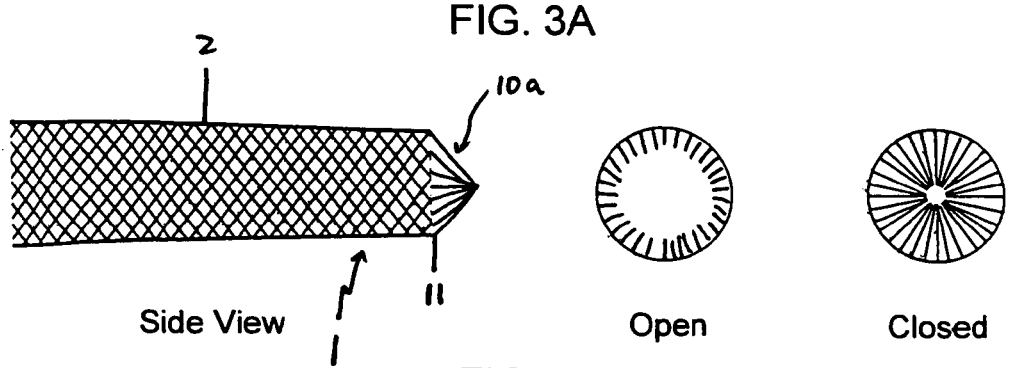
Figure 3C:
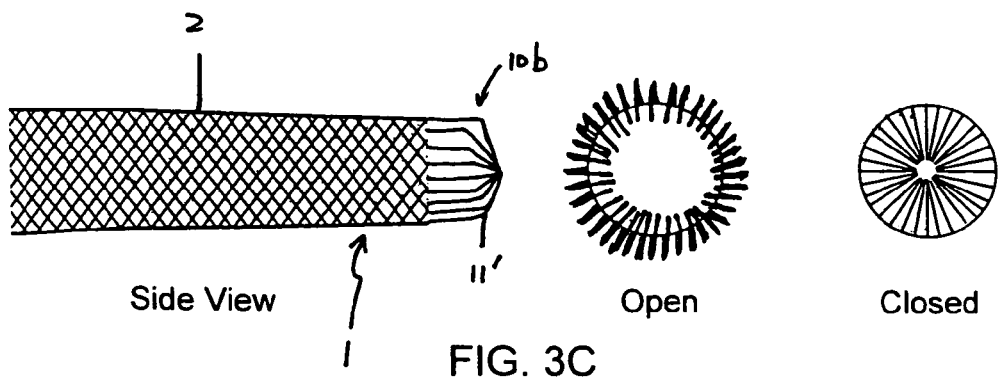

According to another embodiment of the present invention, shown in FIGS. 3B and 3C, the valves 10a, 10b are formed by straightening the distal wires 8 and bending each of the distal wires 8 inwards at a predetermined location 11, 11' of the distal wires 8.

Figure 3D:
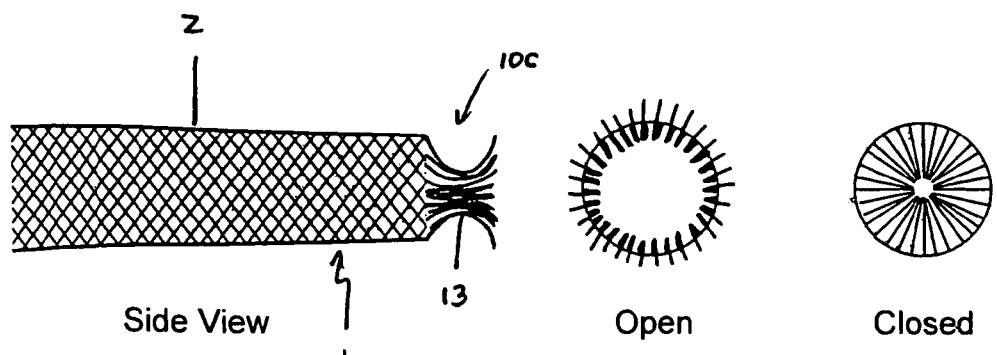

According to still another embodiment of the present invention, shown in FIG. 3D, the valve 10c is formed by curling each of the distal wires 8 outward with the middle portion 13 of each of the distal wires 8 converged toward the center 12 of the circle 14 formed by the tubular body 2 such that each of the bent distal wires 8 forms a U-shaped wire.

The valves 10, 10a, 10b, 10c also may be covered on at least a portion of the valve 10, 10a, 10b, 10c with an elastic covering material to function as a barrier to the reflux. The covering material is selected from a group of polyurethane, silicone, and polytetrafluoroethylene (i.e. teflon), or other suitable materials exhibiting similar characteristics. Preferably, the same material used to cover the tubular portion 2 is used for the valve covering material. The covering 6' of the valves 10, 10a, 10b, 10c may be loose or pleated in order to not inhibit opening and closing of the valve 10, 10a, 10b, 10c.

The right-hand side of FIGS. 3A-3D show cross-sectional views of the valves 10, 10a, 10b, 10c looking down from the cross-sectional plane A-A', which illustrate the open and closed states of the valves 10, 10a, 10b, 10c. The valves 10, 10a, 10b, 10c are normally closed but are configured to open in response to a predetermined condition. The predetermined condition may be a pressure difference between the upstream and the downstream of the valves 10, 10a, 10b, 10c, so that the valves can open while the pressure difference exceeds a certain threshold value, e.g. one induced by a passage of food through into the stomach. The adjustment of the threshold value may be performed, for example, by adjusting the number of distal wires 8 used to form the valves 10, 10a, 10b, 10c. The number of distal wires 8 can be tailored to create a certain amount of spring force that allows the food to pass though the stent 1 into the stomach and also resists the backward reflux pressure. The threshold value also may be adjusted by changing the material of the stent and wires, or the covering. While the valves 10, 10a, 10b, 10c can be configured to be one-way valves, it may be beneficial to allow occasional reverse opening caused by, for example, vomiting, by configuring the valve (e.g. adjusting the spring force required to open the valve) with an appropriate threshold value for a reverse opening.

The length of the valve ranges from 5 to 50 mm, preferably from 10 to 30 mm. The length of the valve is relatively short compared to other types of anti-reflux valves. Therefore, the valve of the present invention requires relatively lower deployment force and, thereby, uses less complex delivery systems.

Figure 1B:
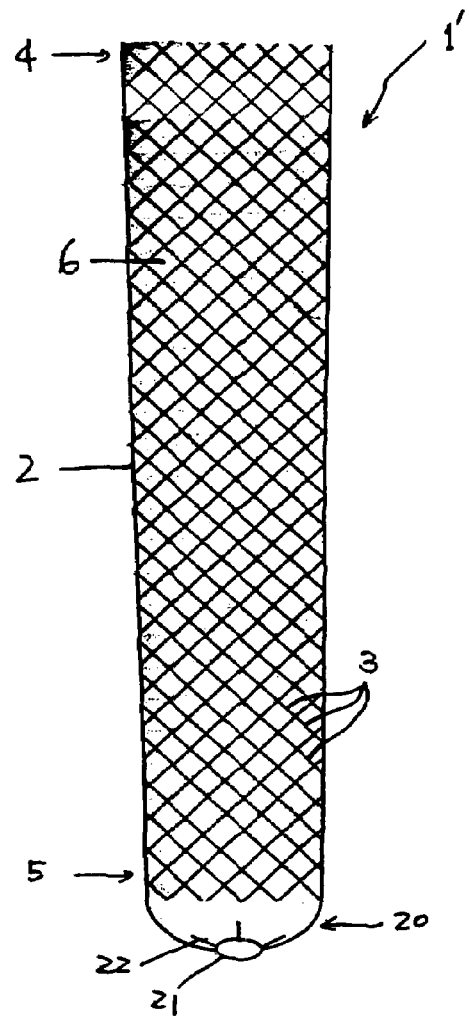

FIG. 1B shows a stent 1' having an elastomeric valve 20 according to still another embodiment of the present invention. In this embodiment, a basket-shaped elastomeric valve 20 made of an elastomeric material is formed integral to the distal end portion of the tubular body 2. Although the tubular body 2 is formed of knitted or braided wires in the exemplary figure, one skilled in the art would recognize that other types of tubular bodies known in the art may also be utilized in the present invention.

The elastomeric valve 20 functions similarly to the valve illustrated in FIG. 1B. The valve 20 is normally closed to prevent acid reflux. but openable for the passage of food from the esophagus into the stomach. At least a portion of the tubular body 2 is provided with strong covering 6 made of an elastic material such as polyurethane, silicone, or polytetrafluoroethylene (i.e. teflon). The valve 20 may be provided with a small opening 21 at the bottom of the valve 20, and the opening 21 may have pleats or cuts 22 to facilitate easy opening of the valve 20. The purpose of the opening 21 is to allow the flow of gas from the stomach up through the esophagus so as to allow a patient to burp and relieve gas pressure in the stomach. However, the opening 21 is small enough to prevent the passage of significant amount of liquid or solid. The diameter of the opening 21 generally ranges from 1 to 10 mm, preferably around 3 mm.

Figure 4:
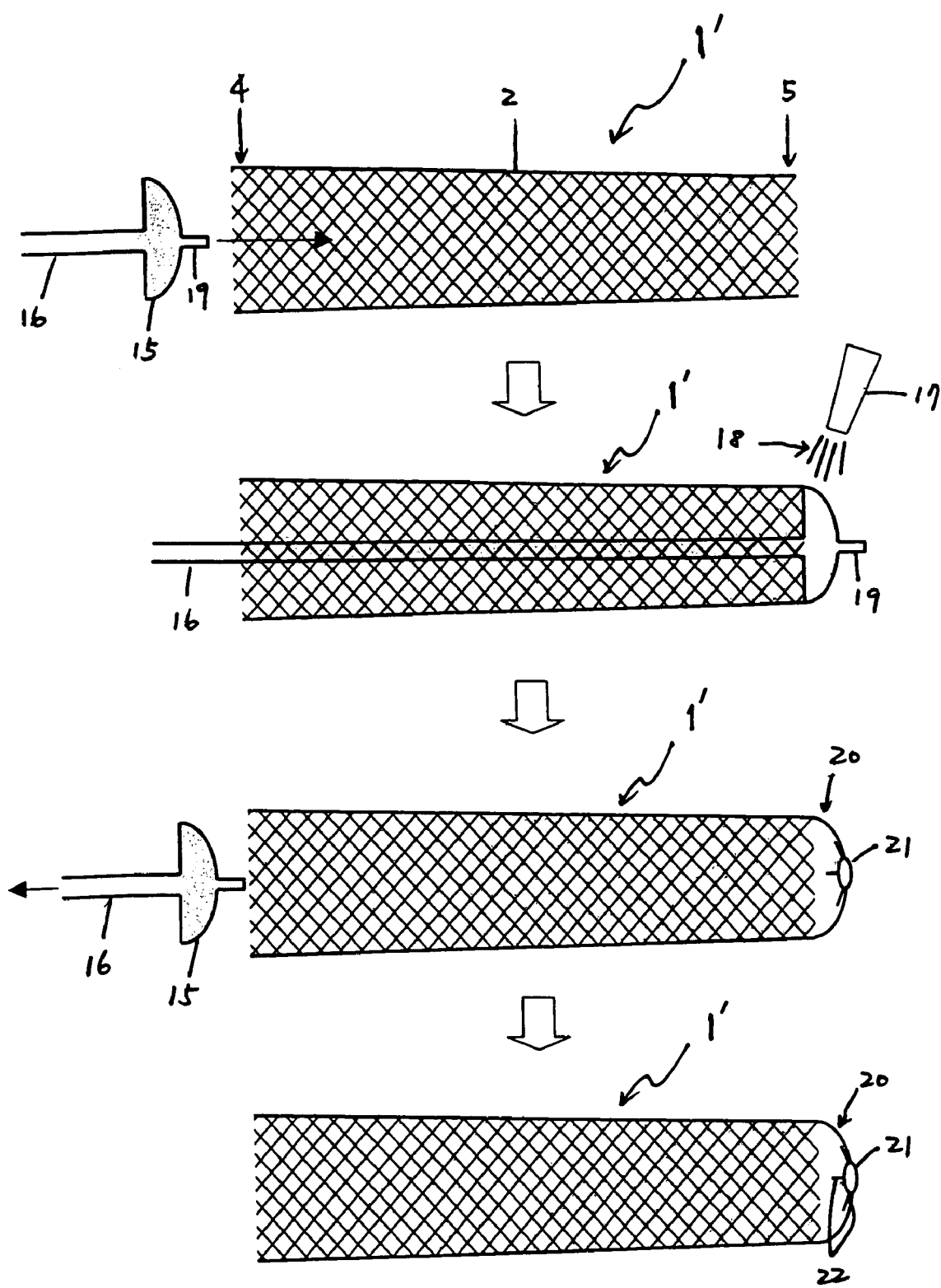
FIG. 4 is a schematic diagram showing a method of manufacturing the embodiment shown in FIG. 1B, according to an embodiment of the present invention.

A method of forming the elastomeric valve 20 is schematically illustrated in FIG. 4. A mold or fixture 15 for a shape of the elastomeric valve 20, preferably basket-shaped, is attached to the distal end portion 5 of the tubular body 2. The fixture 15 is preferably inserted from the proximal end portion 4 with an elongated handle 16. On the surface of the fixture 15, a protrusion 19 is formed to provide a small opening 21 in the elastomeric basket valve 20. Once the fixture 15 is fixed to the tubular body 2, the fixture 15 is coated with an elastomeric material 18, preferably the same material used for covering the tubular body 2 of the stent. The coating can be performed, for example, by spraying 17 or dip-covering (not shown) the elastomeric material 18 onto the surface of the fixture 15. Preferably, this step is performed simultaneously with a step of covering the tubular portion 2 with the covering material 6. After the coating, the elastomeric material 18 coated on the surface of the fixture 15 is cured and the fixture 15 is removed from the stent 1'. The elastomeric valve 20 having the shape of the fixture 15 is thereby formed. Although the exemplary embodiment illustrates the valve 20 attached at the distal end portion, one skilled in the art would recognize that the valve can be formed anywhere in the tubular body 2 between the proximal end portion 4 and the distal end portion 5.

Figure 5:
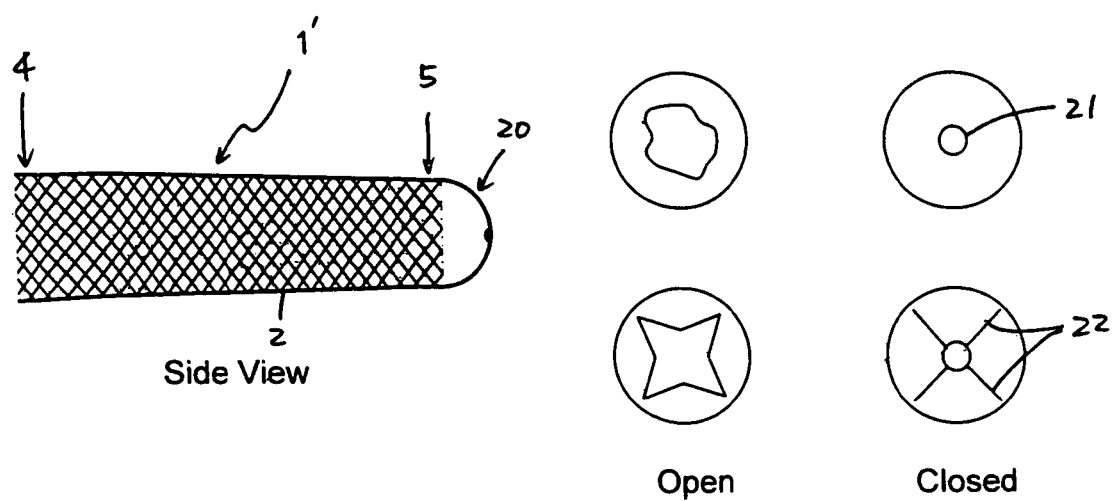
FIG. 5 is side and cross-sectional views of embodiments of medical stents with valves, according to the present invention, showing the open and closed states of the valves.

While the elastomeric valve 20 does not have the structural reinforcement of the wires 3, the valve 20 is relatively rigid and, at the same time, sufficiently elastic to allow it to stretch open while food passes through the stent 1' into the stomach and to spring back and close to prevent the reflux. The valve 20 may be provided with pleats or slits 22 to facilitate opening of the valve 20. FIG. 5 is the side and cross-sectional views of embodiments of medical stents with valves. The upper and lower figures on the right-hand side of in FIG. 5 show the open and closed states of the valve 20 having the opening 21 with and without slits 22, respectively. While the slits 22 facilitate the opening of the valve 20, the valve 20 either with or without the slits 22 on the opening 21 is capable of functioning in the manner described above.

The rigidity and elasticity of the elastomeric valve 20 can be tailored by carefully selecting characteristic parameters, such as the type of elastomeric material 18, coating thickness, number of slits 22, size of hole 21, treatment processes, etc.

Figure 6:
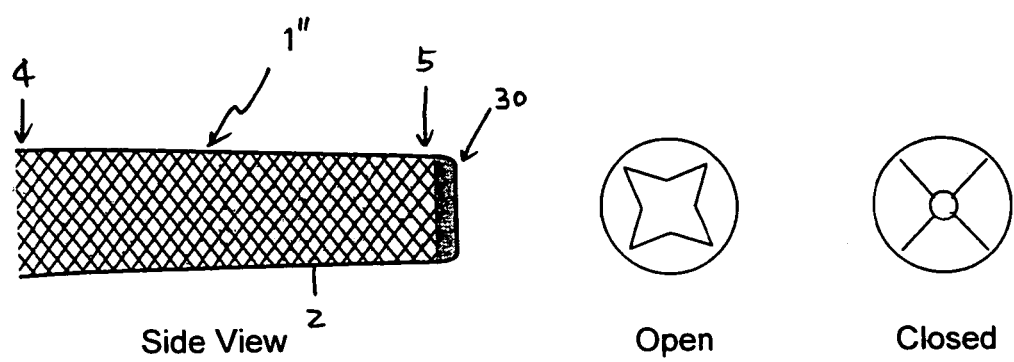
FIG. 6 is side and cross-sectional views of another embodiment of a medical stent with a valve, according to the present invention, showing the open and closed states of the valve.
Figure 2:
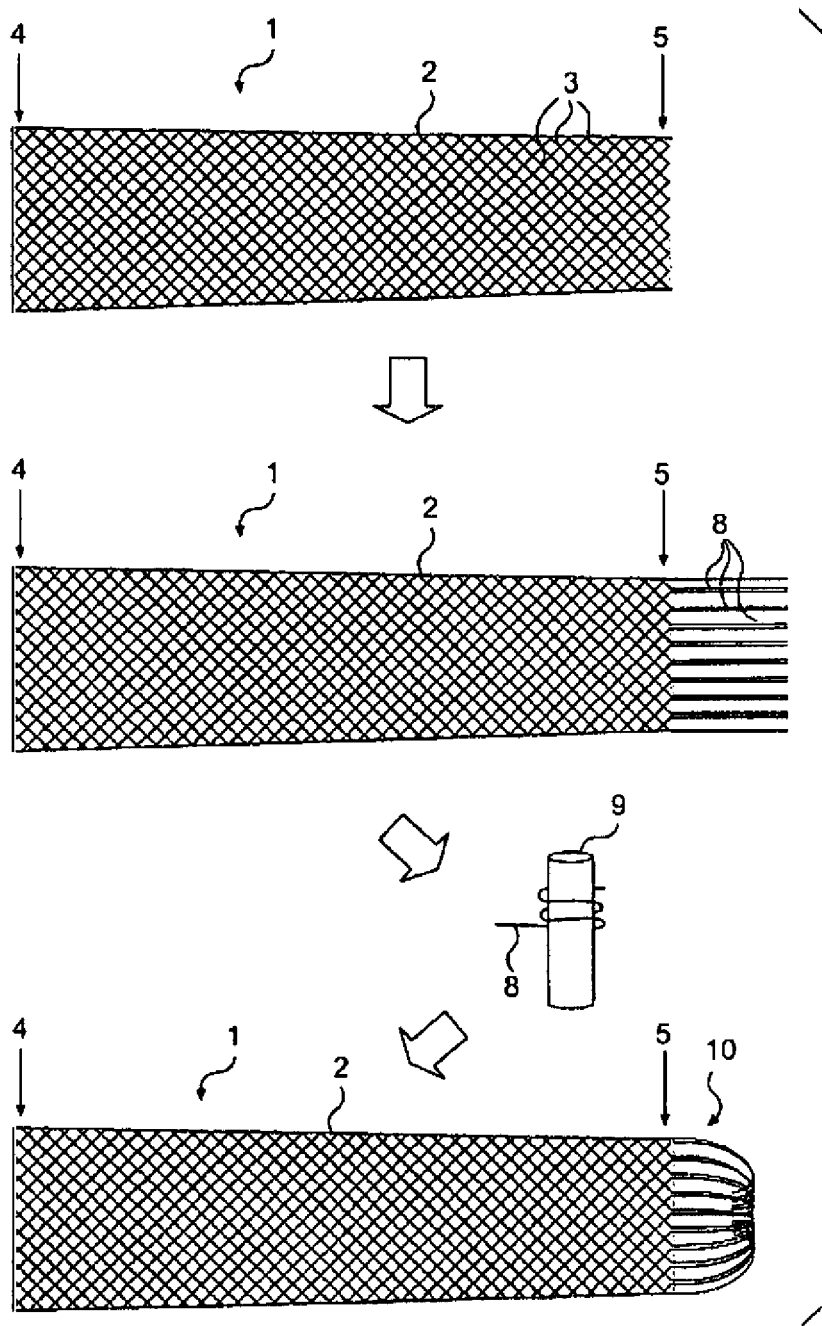
Figure 3A:
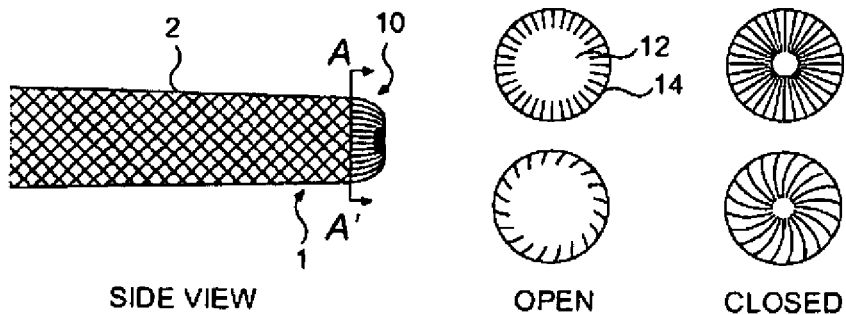
Figure 3B:
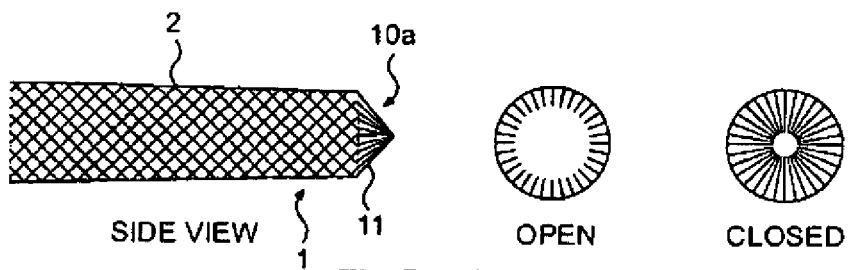
Figure 3C:
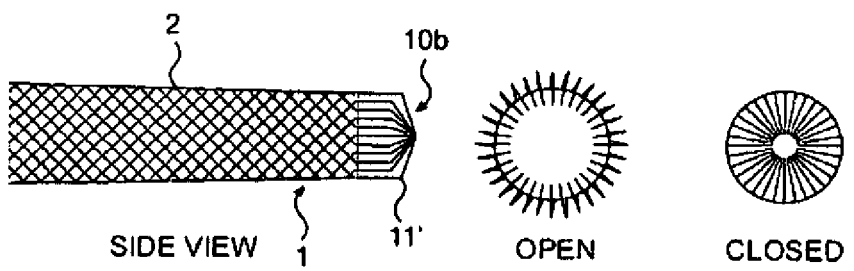
Figure 3D:
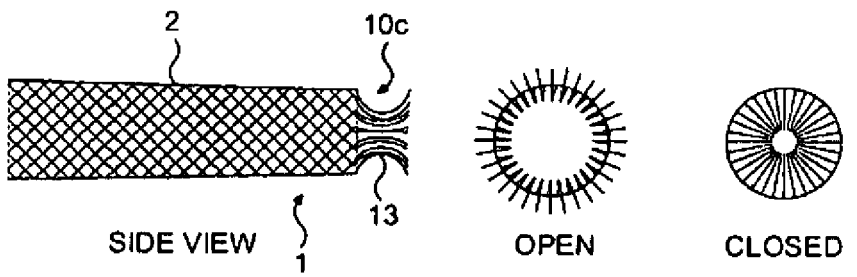
Figure 4:
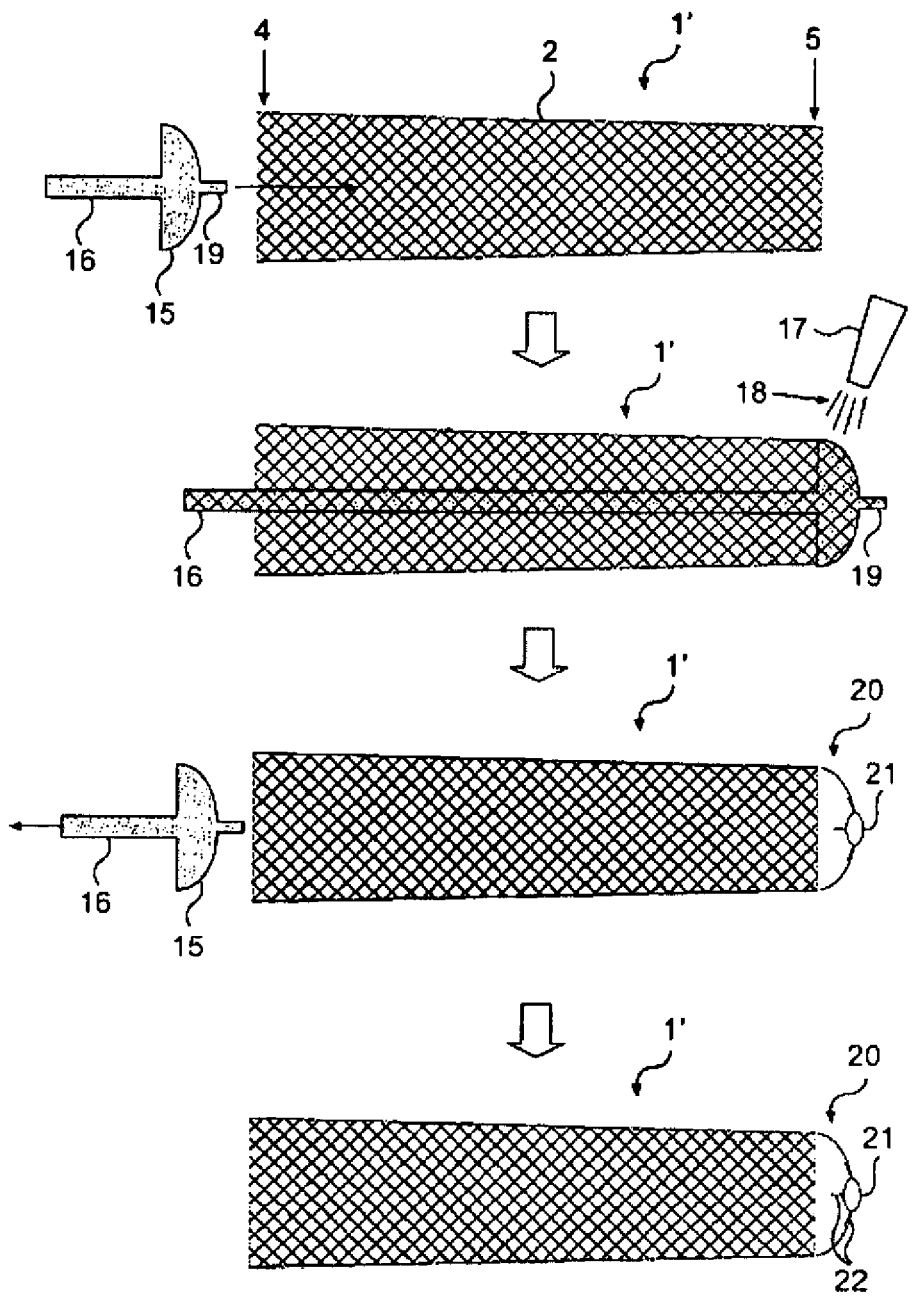
Figure 5:
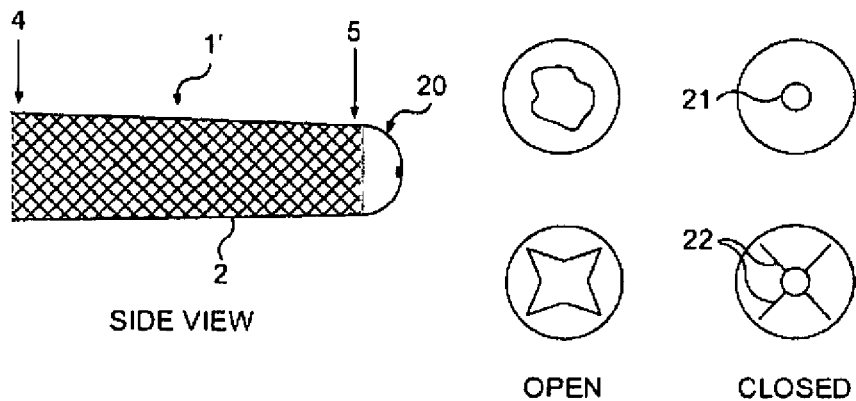
Figure 6:
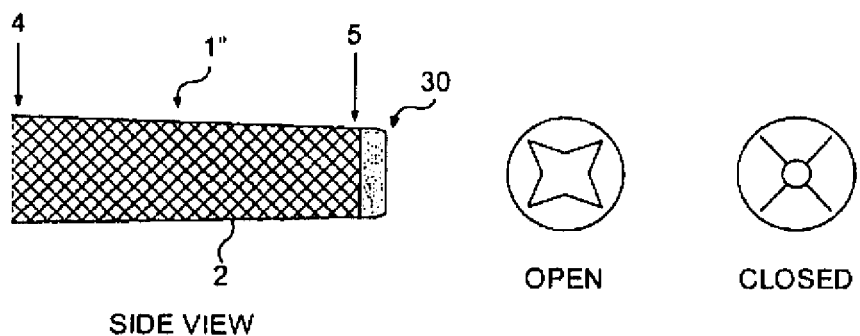

FIG. 6 shows a stent 1" with an integral gasket valve 30 according to still another embodiment of the present invention. The term "gasket valve" is defined as a flat piece of "gasket" material (e.g., a polymer or elastomer) made to function as a valve by providing pleats or cuts in it. In this embodiment, a basket-shaped gasket valve 30 made of an elastomeric material is integrally adhered, sewed, or injection-molded to the distal end portion 5 of the tubular body 2. The integral gasket valve 30 is made of, preferably, the same material 6 used for the tubular portion 2, such as polyurethane, silicone, polytetrafluoroethylene (i.e. teflon), or other suitable material exhibiting similar characteristics.

A flexible gasket valve used in a typical vascular introducer sheath for interventional radiology may be used as the integral gasket valve 30. The integral gasket valve 30 also functions similarly as the basket valves illustrated in FIGS. 1A and 1B, i.e. normally closed to prevent acid reflux but opened for passage of food from the esophagus into the stomach. A small opening 21 is provided at the center of the gasket valve 30 and may be provided with pleats or cuts 22 to facilitate easy opening of the valve 30.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical stent having an elastomeric valve, comprising:
   a generally tubular body formed of braided wires having a proximal end portion and a distal end portion; and
   a normally closed valve made of an elastomeric material and formed integral to the distal end portion of the braided wires, the elastomeric valve having a generally convex outer surface in a normally closed position and is substantially radially symmetric about a longitudinal axis of the tubular body,
   wherein the elastomeric valve is sufficiently rigid so as to substantially maintain a predetermined shape,
   wherein the elastomeric valve is configured to open in response to a predetermined condition, wherein the elastomeric valve includes an opening when the valve is in the normally closed position, and wherein said opening is located at a distal end of the valve.

2. The medical stent according to claim 1, wherein the elastomeric valve is basket-shaped.

3. The medical stent according to claim 1, wherein the elastomeric valve is a gasket valve.

4. The medical stent according to claim 1, wherein at least a portion of the tubular body is provided with a covering.

5. The medical stent according to claim 4, wherein the material for the covering is selected from a group of polyurethane, polytetrafluoroethylene, and silicone.

6. The medical stent according to claim 1, wherein at least a portion of the elastomeric valve is provided with a covering.

7. The medical stent according to claim 6, wherein the material for the covering is selected from a group of polyurethane, polytetrafluoroethylene, and silicone.

8. The medical stent according to claim 7, wherein at least a portion of the tubular body is provided with a covering and a material for the covering in the tubular body is the same as the material for the covering in the elastomeric valve.

9. The medical stent according to claim 1, wherein the predetermined condition is a predetermined pressure difference between an upstream and a downstream of the elastomeric valve.

10. The medical stent according to claim 1, wherein the elastomeric valve is a one-way valve.

11. The medical stent according to claim 1, wherein the opening includes at least one slit.

12. The medical stent according to claim 1, wherein the stent is configured to be placed in an esophagus of a patient.

13. The medical stent according to claim 12, wherein the predetermined condition is a passage of food from the esophagus into the stomach.

14. The medical stent according to claim 12, wherein the predetermined condition is a vomiting of a stomach content from the stomach to the esophagus.

15. The medical stent according to claim 1, wherein the tubular body has a generally tapered body.

16. A medical esophageal stent having an elastomeric valve, comprising:

a generally tubular body having a proximal end portion and a distal end portion, the tubular body being sized and configured to be placed in an esophagus of a patient; and a normally closed valve made of an elastomeric material and formed integral to the distal end portion of the tubular body, the valve having a generally convex outer surface and is substantially radially symmetric about a longitudinal axis of the tubular body wherein the valve is configured to open in response to a predetermined condition, wherein a valved end of the valve includes an opening when the valve is in a normally closed position, and wherein the opening lacks a cover for closing the opening.

17. The medical esophageal stent according to claim 16, wherein at least a portion of the tubular body and valve is provided with a covering.

18. The medical esophageal stent according to claim 17, wherein the material for the covering is selected from a group of polyurethane, polytetrafluoroethylene, and silicone.

19. The medical esophageal stent according to claim 16, wherein the predetermined condition is a predetermined pressure difference between an upstream and a downstream of the valve.

20. The medical esophageal stent according to claim 16, wherein the predetermined condition is a passage of food from the esophagus into the stomach.

21. The medical esophageal stent according to claim 16, wherein the predetermined condition is a vomiting of a stomach content from the stomach to the esophagus.

22. The medical esophageal stent according to claim 16, wherein the valve is a one-way valve.

23. The medical esophageal stent according to claim 16, wherein the tubular body has a generally tapered body.

24. The medical esophageal stent according to claim 16, wherein the elastomeric valve is a gasket valve.

25. The medical esophageal stent according to claim 16, wherein the opening includes at least one slit.

26. The medical esophageal stent according to claim 16, wherein the elastomeric valve is basket-shaped.

27. The medical stent according to claim 1, wherein the elastomeric valve lacks wires.

28. The medical esophageal stent according to claim 16, wherein the tubular body comprises a plurality of flexible wires.

29. The medical esophageal stent according to claim 16, wherein the tubular body comprises an elongate body having a length greater than a diameter of the elongate body.

30. A medical stent having an elastometric valve, comprising:

a generally tubular, radially flexible body having a proximal end portion and a distal end portion; and a normally closed valve made of an elastometric material and formed integral to the distal end portion of the tubular body, the elastometric valve having a generally convex outer surface, wherein the valve is configured to open in response to a predetermined condition, wherein a valve end of the valve includes an opening when the valve is in a normally closed position, and wherein the opening lacks a cover for closing the opening.

31. The medical stent according to claim 30, wherein at least a portion of the tubular body and valve is provided with a covering.

32. The medical stent according to claim 31, wherein the material for the covering is selected from a group of polyurethane, polytetrafluoroethylene, and silicone.

33. The medical stent according to claim 30, wherein the predetermined condition is a predetermined pressure difference between an upstream and a downstream of the valve.

34. The medical stent according to claim 30, wherein the predetermined condition is a passage of food from the esophagus into the stomach.

35. The medical stent according to claim 30, wherein the predetermined condition is a vomiting of a stomach content from the stomach to the esophagus.

36. The medical stent according to claim 30, wherein the valve is a one-way valve.

37. The medical stent according to claim 30, wherein the tubular body has a generally tapered body.

38. The medical stent according to claim 30, wherein the elastomeric valve is a gasket valve.

39. The medical stent according to claim 30, wherein the opening includes at least one slit.

40. The medical stent according to claim 30, wherein the elastomeric valve is basket-shaped.

41. The medical stent according to claim 30, wherein the tubular body comprises a plurality of flexible wires.

42. The medical stent according to claim 30, wherein the tubular body comprises an elongate body having a length greater than a diameter of the elongate body.

43. The medical stent according to claim 30, wherein the tubular body is sized and configured to be placed in an esophagus of a patient.

44. The medical esophageal stent according to claim 16, wherein the body is formed of braded wires and the valve is fixedly attached to the braided wires.

45. The medical stent according to claim 30, wherein the body is formed of braded wires and the valve is fixedly attached to the braided wires.

\* \* \* \* \*

UNITED STATES PATENT AND TRADEMARK OFFICE
CERTIFICATE OF CORRECTION

| | | |
|---|---|---|
| PATENT NO. | : 7,354,455 B2 | |
| APPLICATION NO. | : 10/911650 | |
| DATED | : April 8, 2008 | |
| INVENTOR(S) | : Jonathan Stinson | |

It is certified that error appears in the above-identified patent and that said Letters Patent is hereby corrected as shown below:

In the drawings, Figs 1-6 should be deleted and replaced with the new formal drawing Title page and Figs 1-6 that are attached and should be illustrated.

Claim 16, column 7, line 54, "body wherein" should read --body, wherein--.

Claim 44, column 10, line 2, "braded" should read --braided--.

Claim 45, column 10, line 5, "braded" should read --braided--.

Signed and Sealed this

Eleventh Day of August, 2009

David J. Kappos
*Director of the United States Patent and Trademark Office*

United States Patent
Stinson

(10) Patent No.: US 7,354,455 B2
(45) Date of Patent: *Apr. 8, 2008

(54) MEDICAL STENT WITH A VALVE AND RELATED METHODS OF MANUFACTURING

(75) Inventor: Jonathan S. Stinson, Plymouth, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/911,650

(22) Filed: Aug. 5, 2004

(65) Prior Publication Data
US 2005/0065614 A1 Mar. 24, 2005

Related U.S. Application Data

(63) Continuation of application No. 09/972,054, filed on Oct. 9, 2001, now Pat. No. 6,790,237.

(51) Int. Cl.
*A61F 2/04* (2006.01)
(52) U.S. Cl. ............... 623/23.68; 623/1.24; 623/2.17
(58) Field of Classification Search ............. 623/1.13, 623/1.24, 2.18, 23.68
See application file for complete search history.

(56) References Cited

U.S. PATENT DOCUMENTS

| | | | |
|---|---|---|---|
| 4,339,831 A * | 7/1982 | Johnson | 623/2.18 |
| 4,364,127 A | 12/1982 | Pierce et al. | |
| 4,655,771 A | 4/1987 | Wallsten | |
| 4,846,836 A | 7/1989 | Reich | |
| 5,061,275 A | 10/1991 | Wallsten et al. | |
| 5,314,473 A | 5/1994 | Godin | |
| 5,855,597 A | 1/1999 | Jayaraman | |
| 6,254,642 B1 | 7/2001 | Taylor | |
| 6,264,700 B1 * | 7/2001 | Kilcoyne et al. | 623/23.68 |
| 6,440,164 B1 | 8/2002 | DiMatteo et al. | |
| 6,494,909 B2 | 12/2002 | Greenhalgh | |

(Continued)

FOREIGN PATENT DOCUMENTS

EP   0 808 614 A2   11/1997

(Continued)

OTHER PUBLICATIONS

Kocher, M. et al., "Esophageal Stent with Antireflux Valve for Tumors Involving the Cardia: Work in Progress," Journal of Vascular and Interventional Radiology, vol. 9, No. 6, Nov.-Dec. 1998, pp. 1007-1010.

(Continued)

*Primary Examiner*—Bruce Snow
(74) *Attorney, Agent, or Firm*—Finnegan, Henderson, Farabow, Garrett & Dunner, L.L.P.

(57) ABSTRACT

Medical stents having valves and their methods of manufacture are disclosed. The valve may be basket-shaped and formed integral to a medical stent to prevent undesirable backflow across the valve. The valve can be formed by converting the braided wires of the stent, by providing elastomeric material onto a mold or fixture to form an elastomeric valve, or by attaching a gasket valve. The valve is normally closed but configured to allow easy opening in response to a predetermined condition.

45 Claims, 5 Drawing Sheets

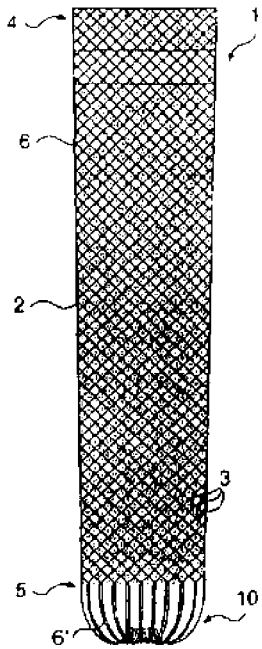

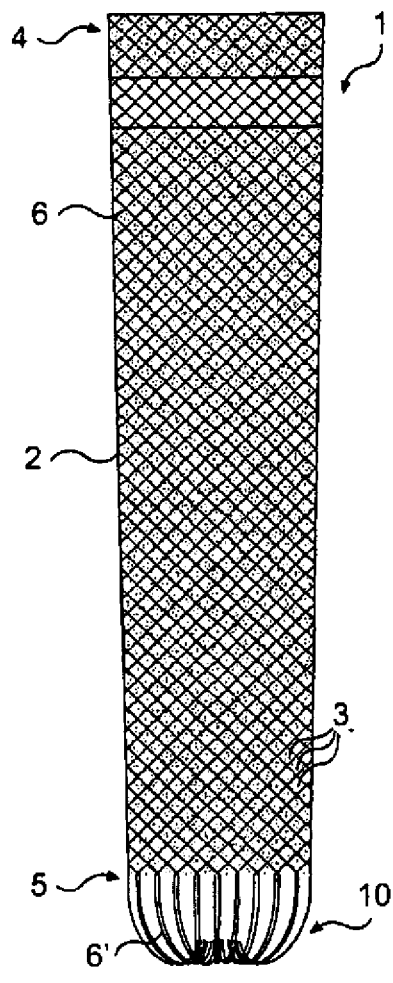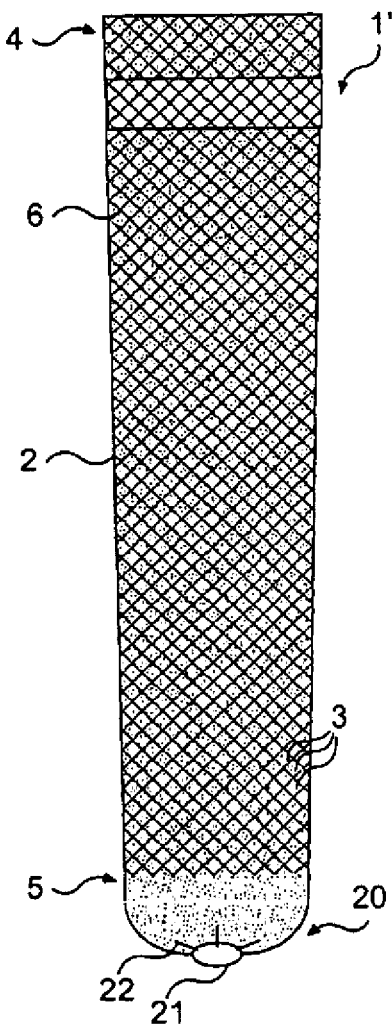
FIG. 1A  FIG. 1B